United States Patent [19]

Bordenca et al.

[11] 3,933,915
[45] Jan. 20, 1976

[54] INSECT REPELLENT COMPOSITIONS AND PROCESS HAVING AN N-SUBSTITUTED HYDROXYALKYL AMINE AS AN ACTIVE INGREDIENT

[75] Inventors: Carl Bordenca, Rocky River, Ohio; Kenneth P. Dorschner, Vienna, Va.; Robert P. Johnson, Baton Rouge, La.

[73] Assignee: SCM Corporation, Cleveland, Ohio

[22] Filed: May 16, 1974

[21] Appl. No.: 470,632

Related U.S. Application Data

[63] Continuation of Ser. No. 265,673, June 23, 1972, abandoned, which is a continuation-in-part of Ser. No. 189,464, Oct. 14, 1971, abandoned.

[52] U.S. Cl. ............................ 260/584 R; 424/325
[51] Int. Cl.$^2$ ................ C07C 91/04; C07C 91/06
[58] Field of Search ........................... 260/584 R

[56] References Cited
OTHER PUBLICATIONS

Ringk et al., J. Am. Chem. Soc. 65, 1222–1223 (1943).
West, Chem. Abstracts, 37 1396$^9$ (1943).

*Primary Examiner*—D. Horwitz
*Attorney, Agent, or Firm*—Merton H. Douthitt; James B. Wilkens

[57] ABSTRACT

Lower hydroxyalkyl amines in which at least one of the amino hydrogens is replaced by an acyclic monoterpenyl radical or hydrogenated acyclic monaterpenyl radical are useful repellents for insect repelling compositions.

5 Claims, No Drawings

INSECT REPELLENT COMPOSITIONS AND PROCESS HAVING AN N-SUBSTITUTED HYDROXYALKYL AMINE AS AN ACTIVE INGREDIENT

This application is a continuation of Ser. No. 265,673, filed June 23, 1972, and now abandoned, which in turn was a continuation-in-part of Ser. No. 189,464, filed Oct. 14, 1971, and now abandoned.

BACKGROUND OF THE INVENTION

This invention relates to compositions containing secondary and tertiary hydroxyalkylamines which are effective insect repellents.

SUMMARY OF THE INVENTION

One aspect of the present invention is our discovery that secondary and tertiary amines of the formula RR′R″N wherein R is a lower hydroxyalkyl radical containing from 2 to 6 carbon atoms, R′ is a acyclic monoterpenyl or hydrogenated acyclic monoterpenyl radical, and R″ is the hydrogen atom or is the same as R′ are effective insect repellents. These hydroxyalkylamine compounds are believed to be novel chemicals.

Another aspect is an insect repellent composition comprising an inert carrier and from about 0.1 to about 90 weight percent of an lower hydroxyalkylamine falling within the class of amines described above and an inert carrier.

A further aspect is a process for repelling insects from a substrate which comprises depositing on or in said substrate an insect repelling proportion of such hydroxyalkylamine. Application dosages are suitably about 5 to 500 mg. per square foot of substrate exposed to insects, and can vary somewhat from this depending upon the degree of repellency desired, the insect to be repelled, the climate, and the expected exposure.

Generally speaking, one important mechanism of activity of insect repellency of compounds resides in their having relatively high vapor pressure; that is, they diffuse into the atmosphere from the substrate or composition in which they are incorporated and are fugitive in character. Thus, the insect repellent activity of an insect repellent compound or composition applied to a substrate is often in the nature of only a few hours' time.

Surprisingly, the compositions of the present invention provide insect activity for prolonged periods of time, even up to one month or longer.

In the foregoing formula R′ is selected from the group consisting of acyclic monoterpenyl radicals and their hydrogenated counterparts. Examples of acyclic monoterpenyl radicals are myrcenyl, linalyl, neryl, citronellyl, bupleuryl, geranyl, lavandulyl, and like radicals. Examples of hydrogenated acyclic terpenyl radicals are 3,7-dimethyloctyl and the like as can be obtained from the acyclic monoterpenyl radicals by partial or complete hydrogenation thereof. The 3,7-dimethyloctyl radical is commonly referred to as the tetrahydrogeranyl radical.

Examples of lower hydroxyalkyl radicals include those residues derived by removing a hydrogen atoms from an unhydroxylated carbon atom in ethanol, n-propanol, i-propanol, n-butanol, secbutyl alcohol, tert-butyl alcohol, 2-methyl-propanol-1, pentanol, and its isomeric alcohols, and hexanol and its isomeric alcohols. The 2-methyl-propanol-1 group sometimes is referred to as 1-hydroxy-2-methyl-2-propyl radical; its connection to the amino nitrogen in the compounds concerned herein can be illustrated by way of example as follows:

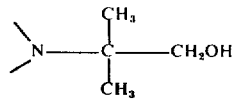

This particular hydroxyalkyl moiety depicted is preferably named as the 2-hydroxy-1,1-dimethylethyl radical in accord with Chemical Abstracts nomenclature when such amino alcohols are named with the amine as the principle component.

Compounds in which R is the 2-hydroxy-1,1dimethylethyl radical have been found to provide particularly advantageous insect repellent compounds.

In the above described process for repelling insects from a substrate which comprises depositing on or in said substrate an insect repelling amount of a lower hydroxyalkylamine, particularly effective for our invention are the compounds substituted with geranyl and geranyl derived groups.

The term "depositing on or in said substrate" is defined as any method of process by which the said repellent is brought into contact with the said substrate either substantially or superficially and includes direct and indirect application to the substrate or surface. Such surfaces include, for example, the bodies of animals and man, growing plants, manufactured products, clothing, webs, and similar devices which might be used in an insect environment. Implied herein are the typical applications, techniques, and formulations commonly employed by those skilled in the use and formulation of insect repellents and pesticides including areas of medicine and veterinary applications to animals and the like and to the locus and surroundings where pesticidal protection is desired. Further, by definition, the term includes the designations contact, deposit, soak, place, permeate, impregnate, invest, coat, treat, surround, cover and like terms. Such deposits would include sprays, lotions, powders, coatings, paints, varnishes, lacquers, and would also imply the finished substrate whether or not other prior or subsequent treatment are commonly made thereto.

Specific compounds which are secondary amines wherein R′ is acyclic monoterpenyl and R″ is H, and which is useful in the practice of this invention include the following listed amines and their neryl, linalyl, and citronellyl counterparts.

N-(2-hydroxyethyl)-geranylamine
N-(2-hydroxypropyl)-geranylamine
N-(2-hydroxy-1-methylethyl)-geranylamine
N-(3-hydroxybutyl)-geranylamine
N-(2-hydroxy-1,1-dimethylethyl)-geranylamine.

Specific compounds which are tertiary amines wherein R′ and R″ are acyclic monoterpenyl and which are useful in the practice of this invention are the following listed amines and their neryl, linalyl, and citronellyl counterparts.

N-(2-hydroxyethyl) digeranylamine
N-(2-hydroxy-1,1-dimethylethyl) digeranylamine
N-(2-hydroxypropyl) digeranylamine
N-(1-hydroxymethyl-propyl) digeranylamine.

Specific secondary amines where R' is tetrahydrogeranyl and R'' is H, and which are useful in the practice of this invention are:

N-(2-hydroxyethyl) 3,7-dimethyloctylamine
N-(2-hydroxy-1,1-dimethylethyl) 3,7-dimethyloctylamine
N-(2-hydroxy-1-methylethyl) 3,7-dimethyloctylamine
N-(2-hydroxybutyl) 3,7-dimethyloctylamine
N-(3-hydroxypropyl) 3,7-dimethyloctylamine.

Specific tertiary amines wherein R' and R'' are fully hydrogenated acyclic monoterpenyl radicals derived by the addition of hydrogen to the unsaturated position of the corresponding neryl, linalyl, citronellyl, and the like compounds described above or from mixtures thereof are:

N-(2-hydroxyethyl) di(3,7-dimethyloctyl)amine
N-(2-hydroxyethyl) di(3,7dimethyloctyl)amine
N-(2-hydroxy-1,1-dimethylethyl) di(3,7-dimethyloctyl)amine.

SYNTHESIS

The compounds of this invention may be prepared by modification of methods well known in the literature. Common general methods for the preparation of substituted aminoalkanols are shown in U.S. Pat. No. 2,363,081 as intermediates for the preparation of various local anesthetic esters and in the Journal of the American Chemical Society publications by Ringk, et al. (65, p. 1222; 1943), Cope, et al. (66 pp. 1733–1747; 1944), Pierce, et al. (71 p. 1765; 1949) among others listed in the prior art references.

Other synthetic approaches occasionally used are preparation of the corresponding amino ketone followed by reduction of the keto group to yield the desired alcohol and hydrogenation of the corresponding oxazolidines as described by Cope and Hancock (J. Am. Chem. Soc. 66, p. 1453; 1944).

A preferred synthetic method for the preparation of the compounds of this invention comprises heating the corresponding acylic monoterpenyl or hydrogenated terpenyl halide with the hydroxy acyclic lower alkylamines such as, for example, 2-hydroxyethylamine, 2-hydroxy-1,1-dimethylethylamine, 2-hydroxypropylamine, and 3-hydroxypropylamine at a temperature in the range from 40° to 160°C. in the presence of an acid acceptor.

If desired an excess of the lower hydroxyalkyl amine can be used as the acid acceptor. The reaction is preferably carried out in an organic solvent inert under the conditions of the reaction. For example, methanol, ethanol, propanol, and higher alcohol and ethers may be used but hydrocarbons such as benzene, xylene, and the like are generally preferred. The acid acceptor generally is a basic substance which forms water soluble by-products with the evolved hydrogen halide which is easily separable from the main reaction product. Alternatives to using an excess of the amine as the hydrogen halide acceptor include the use of tertiary amines such as triethylamine or pyridine. Frequently when a hydrocarbon solvent is used the byproduct amine hydrochloride will be an insoluble solid which can be easily removed from the reaction product by filtration. Work-up in this case is conveniently carried out by filtering the amine hydroclhoride, washing the remaining organic phase with water, evaporating the solvent and distilling the product. In some cases where the products are solids, recrystallization is preferred to distillation.

The hydrogenateed terpenyl compounds also can be prepared by first isolating the terpenyl and the aminoalkanols and subjecting these to hydrogenation procedures commonly used to add hydrogen to unsaturated linkages.

The foregoing compounds range from high-boiling liquids to low-melting solids and have limited water solubility. They can be made water soluble by reacting them with a suitable acid such as, for example, hydrochloric, sulfuric, phosphoric acid, to convert the compounds into the corresponding amine acid salt. Under such circumstances the carrier can be water. It is contemplated that both the hydroxyalkylamine and their water soluble salts will be useful in the practice of this invention.

The novel compounds of this invention are effective in repelling for prolonged periods of time; e.g., up to a month or in some cases longer, a wide spectrum of insects including ticks, flour beetles, moths, house flies, stable and other biting flies such as black flies, horn flies, horse flies, and deer flies, chiggers, ants, cockroaches, mosquitoes, and the like. Typical repellent compositions will contain advantageously between 0.1 and 50 and usually 0.1–25 weight percent of one or more of the compounds herein defined in intimate admixture with a carrier.

The carrier employed can be any carrier conventionally used in insect-repellent formulations with the proviso that the carrier should be inert; that is, it should be incapable of undergoing a chemical reaction with the compound employed. The carrier should also be one that will not be harmful to the environment in which it is employed. Hence intermediates, unreacted excess reactants and reagents, by-products of reaction and solvents containing such generally extraneous chemical material definitely are not a part of the inventive compositions, the latter being fairly commercially pure compounds; e.g., 85% or about with only innocuous diluents, admixed with acceptable carriers for the use. Thus, some agricultural applications can tolerate the common commercially pure admixtures, while applications to animal or human skin demand quite high purities of admixture.

When it is desired to render packaging material, such as for example, boxes, repellent to cockroaches or beetles, the insect-repellent compounds or compositions should be used in sufficient amount to leave an effective layer or residue on the surface of the packaging material. The effective amount of compound to be deposited on the substrate to be made repellent will depend to some extend on the character of carrier used and on the substrate to be protected.

It the repellent is to be applied to a domestic animal such as, for example, a dog to repel biting flies (which are often unaffected by conventional repellents), the carrier should be non-toxic to such animals. Especially preferred are those bland carriers commonly accepted as suitable for veterinary, cosmetic, and medicinal preparations.

Admixtures with non-toxic and non-irritating alcohols, such as isopropanol, hexanols, and other commonly used adjuvants are preferred. Some of the useful adjuvants may themselves possess some measure of repellent activity and such combinations may exhibit synergistic effects providing activity beyond that expected from individual components. Also contemplated in certain repellent usage are combinations of the subject hydroxyalkylamines with which are mixed other useful insecticidally active compounds such as, for example, natural and synthetic pyrethrins. It is expected that the novel compounds of this invention will afford more economical use of such synergizable substances.

The carrier can be any one of a variety of organic or inorganic liquid, solid, or semisolid carriers or carrier formulations conventionally used in the art and can be a mixture of such carriers or carrier formulations.

Examples of liquid hydrocarbon carriers which are widely used for economic reasons include oils produced by the distillation of coal and the distillation of various types and grades of petro-chemical stocks. Petroleum oils which are especially useful and economical include kerosene oils, light and medium agricultural spray oils, and heavy paraffin oils for use in emulsions. Generally preferred are highly refined oils which contain only minute amounts of unsaturated materials as measured by standard sulfonation tests. Such paraffin oils can be emulsified with water and an emulsifier and diluted to lower concentrations and used in conventional aerosol spray devices. Tall oils obtained from the sulfate digestion of wood pulp, like paraffin oils, can also be employed.

In addition to the above-mentioned liquid hydrocarbons, and often employed in conjunction therewith, a carrier can contain conventional emulsifying agents; for example, a nonionic surfactant such as the ethylene oxide condensate of octyphenol or an anionic surfactant such as, for example, an alkali metal salt of an alkylbenzenesulfonic acid. Such emulsifiers permit the composition to be dispersed in and diluted with water for end-use applications.

Paraffin oils are generally employed as carriers in the insect-repellent compositions of this invention, in conjunction with an emulsifier, the mixture being diluted with water immediately prior to end-use application. By way of example, when a compound falling within the scope of the formula hereinbefore described is dissolved in paraffin oil containing an emulsifier and such composition is subsequently diluted with water to form an oil-in-water emulsion, the emulsion when atomized and spraye in insect-infested areas or in areas which are likely to become insect-infested, is a highly effective repellent against such insects and will retain its repellent activity for prolonged periods of time.

Other advantageous organic liquid carriers can include liquid terpene hydrocarbons and terpene alcohols; for example, $\alpha$-pinene, dipentene, terpineol, and the like. Still other liquid carriers can include organic solvents such as volatile aliphatic and aromatic alcohols, esters, aldehydes, and ketones. Aliphatic monohydric alcohols which can be employed inclide methyl, ethyl, n-propyl, isopropyl, n-butyl, sec-butyl, and t-butyl alcohols. Suitable polyhydric alcohols such as ethylene glycol and propylene glycol, glycerine, and the pinacols may be employed.

It is anticipated that creams and lotions containing the novel hydroxyalkylamines of this invention will be preferred applications for human protection against certain insects including mosquitoes. These preparations which will generally contain other adjuvants commonly used in the art may be applied directly to the skin or exposed body portions in humans or animals or, alternatively, be applied to articles of clothing.

The above described repellents can be formulated in creams and lotions using by way of example 0.5 to about 10 parts of the said hydroxyalkylamine in conjunction with about 7 parts dimethyl phthalate and about 3.5 parts magnesium stearate.

Solid carriers which can be used in the compositions include finely divided inorganic solid materials, examples of such materials include finely divided siliceous minerals such as clays; e.g., bentonite, attapulgite, fullers earth, diatomaceous earth, kaolin, mica, talc, finely divided quartz, etc., as well as synthetically prepared siliceous materials including silica aerogels and precipitates and fume silicas. Examples of finely divided solid organic materials include starch, flour, sugar, sawdust, gelatin, and the like.

Examples of semisolid carriers include petroleum jelly, lanolin, and the like and mixtures of liquid and solid carriers which provide semisolid end products.

The above-described compositions can be employed without further dilution, or can be diluted with suitable liquids or solids to repel common insect pests such as roaches, termites, beetles, flies including biting flies, mosquitoes, weevils, moths, ticks, chinch bugs, lice, mites, and the like. Such compositions, when used to contact an insect environment, can effectively repel the insects. By way of example, one advantageous embodiment of a composition of this invention comprises from about 0.1 to 40 percent, preferably 1 to about 25 percent by weight, of a hydroxyalkylamine compound of this invention. Other formulations include up to 10 parts of the lower hydroxyalkylamine, 25 parts dimethyl phthalate, 20 parts white wax, and 50 parts peanut oil.

Granaries and silos can be treated with the compositions of this invention prior to grain storage to prevent beetle, weevil, and other insect infestation in the grain to be subsequently stored.

The following examples are intended to illustrate the invention, but not to limit the scope thereof, parts and percentages being by weight unless otherwise indicated.

EXAMPLE 1

N-(2-hydroxy-1,1-dimethylethyl) Geranylamine

Commercial myrcene hydrochloride, 290 grams (1.12 moles containing about 67% by weight useable geranyl and neryl chlorides) was slowly added with stirring over a 4 hour period to 220 grams (2.25 moles) of molten 2-amino-2-methyl-1-propanol maintained at 55–60°C., and the stirring was continued at this temperature for an additional 2½ hours after completion of the addition. The reaction mixture was made alkaline with 20% aqueous sodium hydroxide and further heated under reflux for 1 hour. After cooling, the organic oil was separated, washed with water, and dried with anhydrous magnesium sulfate. The oil was distilled under vacuum through a short Vigreaux column and the fraction boiling over the range 100°–125°C. at 0.07 mm Hg absolute was collected and identified as 99% pure N-(2-hydroxy-1,1-dimethylethyl) geranylamine (41% yield). NMR spectroscopy identified the product as a mixture containing both the geranyl and neryl isomers.

EXAMPLE 2

N-(2-hydroxy-1,1-dimethylethyl) Digeranylamine

The vacuum distillation described in Example 1 was continued after removing the monogeranylamine. After discarding an intermediate fraction, N-(2-hydroxy-1,1-dimethylethyl) digeranylamine was isolated in 21% yield, b.p. 170°–190° at 0.07 mm Hg absolute. NMR spectroscopy showed this fraction to be 98% pure (mixture of both digeranyl and dineryl isomers).

EXAMPLE 3

N-(2-hydroxy-1,1-dimethylethyl) Tetrahydro-Geranylamine

A solution of 20 grams of N-(2-hydroxy-1,1-dimethylethyl) geranylamine in 25 milliliters of glacial acidic acid was treated with 0.4 grams of platinum oxide ("Adams catalyst") and subjected to hydrogenation at 60 psi hydrogen pressure for three hours. The resultant solution was filtered to remove the catalyst, diluted with aqueous sodium hydroxide and the crude product was allowed to solidify. The crude product when recrystallized for acetone yielded a white solid, melting at 59°–61°C. Alternatively, purification could be effected by distillation under reduced pressure (b.p. 108°–155°C. at 0.17 mm Hg absolute). The structure of the product was verified by NMR spectroscopy.

EXAMPLE 4

N-(2-hydroxyethyl) geranylamine was prepared in a manner similar to the procedure of Example 1 except that the alcohol used was 2-aminoethanol.

EXAMPLE 5

N-(2-hydroxyethyl digeranylamine was prepared in a manner similar to the procedure described in Example 2 after isolating the compound described in Example 4.

EXAMPLE 6

N-(2-hydroxypropyl) geranylamine was prepared in a manner similar to the procedure of Example 1 except that amino alcohol used was 2-hydroxypropylamine.

EXAMPLE 7

N-(2-hydroxypropyl) digeranylamine was obtained as a higher boiling fraction after isolating the compound of Example 6 in that process.

EXAMPLE 8

N-(1-hydroxymethyl-propyl) 3,7-dimethyloctylamine was prepared in a manner similar to the procedure of Example 3 except that the starting material used was N-(1-hydroxymethyl-propyl) geranylamine.

EXAMPLE 9

Two separate acetone solutions were prepared. Each solution contained 1.5 weight percent of one of the following compounds:
N-(2-hydroxyethyl)digeranylamine
N-(2-hydroxyethyl)geranylamine.

Each solution was used to treat two sheets of brown kraft paper, and the sheets were treated with an amount of solution sufficient to obtain a concentration of 20 mg. of compound per square foot of paper. The test solutions were applied to the paper sheets and allowed to dry overnight, after which they were cut into strips having a 6-inch by 12-inch length for test purposes.

The long edges of a treated and untreated piece of kraft paper of the same dimensions were joined with transparent tape. Plastic cylinders were placed over the treated and untreated papers so that the joined edges constituted the diameter of the test cylinder. Mineral oil was applied to the walls of the plastic cylinders to force the insects onto the paper surface. The test insect was the confused flour beetle (*Tribolium confusum*), and 3-inch diameter cylinders were employed. Untreated control sheets were provided as a negative control, and a standard sheet which had been treated with acetone solutions of 2-hydroxyethyl-n-octylsulfide, applied to kraft paper sheets at the same level were used as the standard positive control. Results are given in Table I. Ten insects were used in each cylinder.

The number of insects on the treated and untreated surfaces of the paper were recorded at one-hour intervals. The percent repellency was determined by the formula u−t/u × 100
where "u" is the number of insects on the untreated paper, and "t" is the number of insects on the treated paper. As is evident from the table, N-(2-hydroxyethyl)digeranylamine was substantially equivalent to the standard, and the N-(2-hydroxyethyl)geranylamine was significantly above the standard. Four replicate tests were run for each compound and the controls.

TABLE I

| Chemical Treatment | Rep. Nos. | Observation Periods — Hours* | | | | | | | | Total Count | | Percent Repellency |
| | | 1.0 | | 2.0 | | 3.0 | | 4.0 | | | | |
| | | T | U | T | U | T | U | T | U | T | U | |
| --- | --- | --- | --- | --- | --- | --- | --- | --- | --- | --- | --- | --- |
| N-(2-hydroxyethyl)Digeranylamine | 1 | 1 | 9 | 0 | 10 | 0 | 10 | 0 | 10 | | | |
| | 2 | 1 | 9 | 0 | 10 | 1 | 9 | 0 | 10 | | | |
| | 3 | 5 | 5 | 0 | 10 | 0 | 10 | 0 | 10 | | | |
| | 4 | 4 | 6 | 0 | 10 | 0 | 10 | 0 | 10 | 12 | 148 | 92 |
| N-(2-hydroxyethyl)Geranylamine | 1 | 0 | 10 | 0 | 10 | 0 | 10 | 0 | 10 | | | |
| | 2 | 0 | 10 | 0 | 10 | 0 | 10 | 0 | 10 | | | |
| | 3 | 0 | 10 | 0 | 10 | 0 | 10 | 0 | 10 | | | |
| | 4 | 0 | 10 | 0 | 10 | 0 | 10 | 0 | 10 | 0 | 160 | 100 |
| 2-Hydroxyethyl n-octyl sulfide (Standard) | 1 | 0 | 10 | 0 | 10 | 0 | 10 | 1 | 9 | | | |
| | 2 | 0 | 10 | 0 | 10 | 0 | 10 | 0 | 10 | | | |
| | 3 | 1 | 9 | 1 | 9 | 0 | 10 | 0 | 10 | | | |
| | 4 | 4 | 6 | 0 | 10 | 0 | 10 | 1 | 9 | 8 | 152 | 95 |
| Untreated | 1 | 7 | 3 | 3 | 7 | 4 | 6 | 1 | 9 | | | |
| | 2 | 4 | 6 | 9 | 1 | 3 | 7 | 9 | 2 | | | |
| | 3 | 7 | 3 | 0 | 10 | 9 | 1 | 8 | 2 | | | |
| | 4 | 1 | 9 | 8 | 2 | 4 | 6 | 5 | 5 | 81 | 79 | — |

*T= Treated;
U= Untreated specimens

EXAMPLE 10

The procedure of Example 9 was repeated with an amount of solution sufficient to obtain a concentration of 14 milligrams of compound per square foot of paper except that N-(2-hydroxy-1,1-dimethylethyl) geranylamine and N-(2-hydroxy-1,1-dimethylethyl) digeranylamine were employed in place of the compounds employed in Example 9. The results given in Table II demonstrate that these products equal or surpass the insect repellency provided by the control.

EXAMPLE 12

The procedure of Example 9 was repeated to determine test duplicability of 14 milligrams of compound per square foot of paper in all instances. The results are set forth in Table IV and shown that the two compounds employed; i.e., N-(2-hydroxy-1,1-dimethylethyl) geranylamine and N-(2-hydroxy-1,1-dimethylethyl) digeranylamine, are again equivalent to or better than the standard control.

TABLE IV

| Chemical Treatment | Rep. Nos. | Observation Periods — Hours* | | | | | | | | Total Count | | Percent Repellency |
| --- | --- | --- | --- | --- | --- | --- | --- | --- | --- | --- | --- | --- |
| | | 1.0 | | 2.0 | | 3.0 | | 4.0 | | | | |
| | | T | U | T | U | T | U | T | U | T | U | |
| N-(2-hydroxy-1,1-dimethyl- | 1 | 0 | 10 | 0 | 10 | 1 | 9 | 2 | 8 | | | |
| ethyl) geranylamine | 2 | 0 | 0 | 0 | 10 | 0 | 10 | 2 | 8 | | | |
| | 3 | 0 | 10 | 0 | 10 | 0 | 10 | 1 | 9 | | | |
| | 4 | 0 | 10 | 0 | 10 | 0 | 10 | 0 | 10 | 6 | 154 | 96 |
| N-(2-hydroxy-1,1-dimethyl- | 1 | 0 | 10 | 0 | 10 | 0 | 10 | 1 | 9 | | | |
| ethyl) Digeranylamine | 2 | 0 | 10 | 0 | 10 | 0 | 10 | 1 | 9 | | | |
| | 3 | 0 | 10 | 0 | 10 | 0 | 10 | 0 | 10 | | | |
| | 4 | 0 | 10 | 0 | 10 | 0 | 10 | 0 | 10 | 2 | 158 | 99 |
| 2-hydroxyethyl-n-octyl- | 1 | 1 | 9 | 5 | 5 | 0 | 10 | 0 | 10 | | | |
| sulfide (Standard) | 2 | 1 | 9 | 0 | 10 | 1 | 9 | 1 | 9 | | | |
| | 3 | 0 | 10 | 0 | 10 | 1 | 9 | 1 | 9 | | | |
| | 4 | 0 | 10 | 0 | 10 | 0 | 10 | 0 | 10 | 11 | 149 | 93 |

*T = Treated; U= Untreated

TABLE II

| Chemical Treatment | Rep. Nos. | Observation Periods — Hours | | | | | | | | Total Count | | Percent Repellency |
| --- | --- | --- | --- | --- | --- | --- | --- | --- | --- | --- | --- | --- |
| | | 1.0 | | 2.0 | | 3.0 | | 4.0 | | | | |
| | | T | U | T | U | T | U | T | U | T | U | |
| N-(2-hydroxy-1,1-dimethyl- | 1 | 0 | 10 | 0 | 10 | 0 | 10 | 0 | 10 | | | |
| ethyl) Geranylamine | 2 | 0 | 10 | 0 | 10 | 0 | 10 | 0 | 10 | | | |
| | 3 | 0 | 10 | 0 | 10 | 0 | 10 | 0 | 10 | | | |
| | 4 | 0 | 10 | 0 | 10 | 0 | 10 | 0 | 10 | 0 | 160 | 100 |
| N-(2-hydroxy-1,1-dimethyl- | 1 | 6 | 4 | 1 | 9 | 0 | 10 | 0 | 10 | | | |
| ethyl)Digeranylamine | 2 | 1 | 9 | 0 | 10 | 0 | 10 | 1 | 9 | | | |
| | 3 | 1 | 9 | 0 | 10 | 0 | 10 | 0 | 10 | | | |
| | 4 | 0 | 10 | 0 | 10 | 0 | 10 | 0 | 10 | 10 | 150 | 93 |
| 2-Hydroxyethyl-n-octylsulfide | 1 | 0 | 10 | 0 | 10 | 0 | 10 | 1 | 9 | | | |
| (Standard) | 2 | 0 | 10 | 0 | 10 | 0 | 10 | 0 | 10 | | | |
| | 3 | 1 | 9 | 0 | 10 | 0 | 10 | 0 | 10 | | | |
| | 4 | 4 | 6 | 0 | 10 | 0 | 10 | 1 | 9 | 8 | 152 | 95 |
| Untreated | 1 | 7 | 3 | 3 | 7 | 4 | 6 | 1 | 9 | | | |
| | 2 | 4 | 6 | 9 | 1 | 3 | 7 | 8 | 2 | | | |
| | 3 | 7 | 3 | 0 | 10 | 9 | 1 | 8 | 2 | | | |
| | 4 | 1 | 9 | 8 | 2 | 4 | 6 | 5 | 5 | 81 | 79 | — |

EXAMPLE 11

The procedure of Example 9 was repeated except that the kraft paper strips were treated with an amount of material equal to 7 milligrams per square foot of kraft paper, and the same compounds were employed. The results are given in Table III.

EXAMPLE 13

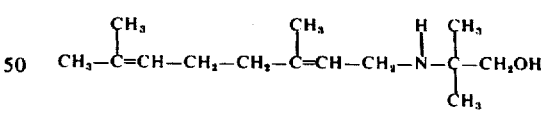

N-(2-hydroxy-1,1-dimethylethyl) geranylamine was screened for its repellent activity against the German

TABLE III

| Chemical Treatment | Rep. Nos. | Observation Periods — Hours | | | | | | | | Total Count | | Percent Repellency |
| --- | --- | --- | --- | --- | --- | --- | --- | --- | --- | --- | --- | --- |
| | | 1.0 | | 2.0 | | 3.0 | | 4.0 | | | | |
| | | T | U | T | U | T | U | T | U | T | U | |
| N-(2-hydroxy-1,1-dimethyl- | 1 | 1 | 9 | 1 | 9 | 1 | 9 | 0 | 10 | | | |
| ethyl) Geranylamine | 2 | 0 | 10 | 1 | 9 | 2 | 8 | 2 | 8 | | | |
| | 3 | 0 | 10 | 4 | 6 | 0 | 10 | 5 | 5 | | | |
| | 4 | 8 | 2 | 7 | 3 | 1 | 9 | 2 | 8 | 35 | 125 | 72 |
| N-(2-hydroxy-1,1-dimethyl- | 1 | 5 | 5 | 0 | 10 | 0 | 10 | 1 | 9 | | | |
| ethyl)Digeranylamine | 2 | 2 | 8 | 0 | 10 | 1 | 9 | 2 | 8 | | | |
| | 3 | 8 | 2 | 0 | 10 | 1 | 9 | 1 | 9 | | | |
| | 4 | 5 | 5 | 0 | 10 | 1 | 9 | 6 | 4 | 33 | 127 | 74 |
| Untreated | 1 | 2 | 8 | 7 | 3 | 4 | 6 | 2 | 8 | | | |
| | 2 | 8 | 2 | 6 | 4 | 2 | 8 | 9 | 1 | | | |
| | 3 | 1 | 9 | 5 | 5 | 7 | 3 | 0 | 10 | | | |
| | 4 | 10 | 0 | 3 | 7 | 5 | 5 | 4 | 6 | 75 | 85 | 12 | cockroach *Blattella germanica* using the following procedure:

Five milliliters of a 2.0 percent solution of N-(2-hydroxy-1,1-dimethylethyl) geranylamine in acetone was applied to the inside of a one-half pint, cylindrical paperboard carton. An opening ¾ inch in diameter was cut into the carton to give the roaches access to food and water which were placed inside. The treated carton was placed in the center of a 10-inch evaporating dish having side walls greased to prevent escape. Twenty-five adult roaches were placed in the dish. The number of roaches found in the treated carton as well as the number of roaches in the control carton which has been treated with acetone only was observed at daily intervals. The effectiveness is based on the length of time elapsing before 50 percent or more of the insects consistently entered the treated carton. The dead insects were replaced at least 24 hours before a count was made. All tests were run in duplicate. The data in Table V show that N-(2-hydroxy-1,1-dimethylethyl) geranylamine is effective for at least 4 days under test conditions.

TABLE V

Insect Repellency to Blattella germanica
USDA House Test

| Chemical Treatment | % Roaches inside treated cartons on indicated days after treatment | |
|---|---|---|
| | 2 | 4 |
| N-(2-hydroxy-1,1-dimethyl-ethyl)geranyl amine | 0 | 36 |
| None | 96 | 92 |

EXAMPLE 14

N-(2-hydroxy-1-propyl) digeranylamine was evaluated for effectiveness against *Blattella germanica* using a procedure described in the preceding example. The test indicates that this compound repels the German cockroach effectively for 4 days.

EXAMPLE 15

N-(2-hydroxy-1-propyl) geranylamine was screened for its effectiveness against *Blattella germanica* using the procedure described in Example 13. The results indicate that this compound is effective for 6 days under the conditions of the tests. The test was repeated using the same procedure hereinbefore described except that the treated carton was aged for 6 days before testing, and the compound was shown to be effective for an additional 7 days.

EXAMPLE 16

The procedure of the preceding example was repeated except that the paperboard cylinders were treated and aged for 10 days prior to testing and the material; i.e., N-(2-hydroxy-1,1-dimethylethyl) 3,7-dimethyl-1-octylamine, was found to be an effective repellent for over twelve days thereafter.

EXAMPLE 17

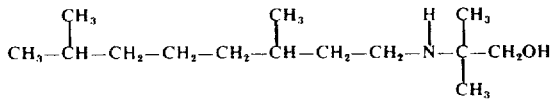

The procedure of the preceding example was repeated except that 80 milligrams of N-(2-hydroxy-1,1-dimethylethyl) 3,7-dimethyl-1-octylamine per square foot of inside carton surface was employed and the treated materials were aged for 15 days before testing at this level. The compound was found to be still effectively repellent after 24 days.

EXAMPLE 18

The procedure of Example 9 was repeated except that the compound N-(2-hydroxy-1,1-dimethylethyl) 3,7-dimethyl-1-octylamine was tested against the flour beetle *Tribolium confusum*. The compound was placed on paper in an acetone carrier in a manner to deposit 16 milligrams of compound per square foot of brown kraft paper. The results given in Table VI show the percent repellency to be 92 percent.

TABLE VI

| | | Observation Periods — Hours* | | | | | | | | | |
|---|---|---|---|---|---|---|---|---|---|---|---|
| | Rep. | 1.0 | | 2.0 | | 3.0 | | 4.0 | | Total Count | Percent |
| Chemical Treatment | Nos. | T | U | T | U | T | U | T | U | T | U | Repellency |
| N-(2-hydroxy-1,1-diemthyl- | 1 | 0 | 10 | 0 | 10 | 0 | 10 | 0 | 10 | | | |
| ethyl)3,7-dimethyl-1-octyl- | 2 | 0 | 10 | 0 | 10 | 0 | 10 | 0 | 10 | | | |
| amine | 3 | 6 | 4 | 0 | 10 | 0 | 10 | 0 | 10 | | | |
| | 4 | 6 | 4 | 0 | 10 | 0 | 10 | 0 | 10 | 12 | 148 | 92 |
| Untreated | 1 | 9 | 1 | 3 | 7 | 6 | 4 | 9 | 1 | | | |
| | 2 | 0 | 10 | 8 | 2 | 6 | 4 | 9 | 1 | | | |
| | 3 | 9 | 1 | 7 | 3 | 9 | 1 | 0 | 10 | | | |
| | 4 | 1 | 9 | 7 | 3 | 3 | 7 | 7 | 3 | 92 | 68 | 0 |

*T = Treated;
U = Untreated

EXAMPLE 19

1.5 grams of N-(2-hydroxy-1,1-dimethylethyl) 3,7-dimethyl-1-octylamine dissolved in acetone was used to treat 1 square foot of two cotton stockings. The same amount of the standard commercially available, N,N-diethyl-m-toluamide, was used to treat two additional stockings. The treatments were exposed to caged mosquitoes and stable flies by pulling the stockings over the forearm of a human technician and inserting the arm into the cage. The procedure was repeated until five bites were received in a 1-minute exposure of treatment. The insects used in this repellency experiment were yellow fever mosquitoes, *Aedes aegypti*, and the stable flies *Stomoxys calcitrans*. The results are given in Table VII.

TABLE VII

| Compound | Protection Time in Weeks | |
|---|---|---|
| | Stable Flies | Mosquitoes |
| N-(2-hydroxy-1,1-dimethylethyl) 3,7-dimethyl-1-octylamine | 13 | 5 |
| N,N-diethyl-m-toluamide Control | 5 | 5 |

The results show that the test compound protected the arms from bites for a period of 13 weeks in the case of stable flies and for 5 weeks in the case of the mosquitoes. The standard protected the arm against bites for stable flies and mosquitoes for 5 weeks in each instance.

What is claimed is:

1. A hydroxyalkyl amine selected from the group consisting of: N-(2-hydroxy-1,1-dimethylethyl)-di(3,7-dimethyloctyl) amine, N-(2-hydroxy-1,1-dimethylethyl) geranyl amine, N-(2-hydroxy-1,1-dimethylethyl) digeranyl amine, and N-(2-hydroxyethyl) geranyl amine.

2. N-(2-hydroxy-1,1-dimethylethyl) di(3,7-dimethyloctyl) amine.

3. N-(2-hydroxy-1,1-dimethylethyl)geranyl amine.

4. N-(2-hydroxy-1,1-dimethylethyl) digeranyl amine.

5. N-(2-hydroxyethyl) geranyl amine.

* * * * *

UNITED STATES PATENT OFFICE
CERTIFICATE OF CORRECTION

Patent No. 3,933,915  Dated  January 20, 1976

Inventor(s) Carl Bordenca et al.

It is certified that error appears in the above-identified patent and that said Letters Patent are hereby corrected as shown below:

Abstract, line 3, change "monaterpenyl" to read "monoterpenyl".
Column 1, line 49, after "insect", insert --repellent--.
Column 3, line 19, delete "N-(2-hydroxyethyl) di(3,7dimethyloctylamine"; line 66, change "hydroclhoride" to read "hydrochloride".
Column 4, line 4, after "terpenyl", delete "and the"; line 36, change "and", first occurrence to read -- or --;
line 53, change "extend" to read "extent"; line 67, after "providing", insert --repellent--.
Column 5, line 46, change "spraye" to read "sprayed".
Column 7, line 25, change "for" to "from".
Columns 9 and 10, Table IV, under 1.0-U, opposite "ethyl) geranylamine", change "0" to "10".
Column 11, Table VI, change "N-(2-hydroxy-1,1-diemthylethyl)3,7-dimethyl-1-octylamine"to read "N-(2-hydroxy-1,1-dimethylethyl)3,7-dimethyl-1-octylamine".
Column 13, line 2, change "for" to read "by".

Signed and Sealed this eleventh Day of May 1976

[SEAL]

Attest:

RUTH C. MASON
Attesting Officer

C. MARSHALL DANN
Commissioner of Patents and Trademarks